US012208211B2

(12) United States Patent
Garcia et al.

(10) Patent No.: US 12,208,211 B2
(45) Date of Patent: Jan. 28, 2025

(54) SYSTEMS AND METHODS FOR SUSTAINED BREATH DELIVERY TO NEONATES

(71) Applicant: GE Precision Healthcare LLC, Wauwatosa, WI (US)

(72) Inventors: Daniel Garcia, Wauwatosa, WI (US); Ramune Auzelyte, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 623 days.

(21) Appl. No.: 17/435,329

(22) PCT Filed: Apr. 17, 2020

(86) PCT No.: PCT/US2020/028759
§ 371 (c)(1),
(2) Date: Aug. 31, 2021

(87) PCT Pub. No.: WO2020/219360
PCT Pub. Date: Oct. 29, 2020

(65) Prior Publication Data
US 2022/0134044 A1    May 5, 2022

Related U.S. Application Data

(60) Provisional application No. 62/839,383, filed on Apr. 26, 2019.

(51) Int. Cl.
*A61M 16/08* (2006.01)
*A61M 16/00* (2006.01)
(Continued)

(52) U.S. Cl.
CPC ...... *A61M 16/0833* (2014.02); *A61M 16/024* (2017.08); *A61M 16/06* (2013.01);
(Continued)

(58) Field of Classification Search
CPC .............. A61M 16/0833; A61M 16/06; A61M 16/201–207; A61M 2240/00
See application file for complete search history.

(56) References Cited

U.S. PATENT DOCUMENTS 4,502,481 A * 3/1985 Christian ............... A61M 16/00
128/205.24
5,557,049 A * 9/1996 Ratner ..................... G01L 7/084
73/756
(Continued)

FOREIGN PATENT DOCUMENTS

WO    2014195511 A1    12/2014
WO    2016119006 A1    8/2016

OTHER PUBLICATIONS

International Search Report and Written Opinion for International Application PCT/US20/28759 mailed Jul. 29, 2020.
(Continued)

*Primary Examiner* — Joseph D. Boecker
*Assistant Examiner* — Thomas W Greig
(74) *Attorney, Agent, or Firm* — Andrus Intellectual Property Law, LLP

(57) ABSTRACT

A T-piece for ventilating a neonate includes a body having three ports, including an air supply connection port configured to connect to an air supply hose to receive gas therefrom, a mask connection port configured to connect to a neonatal ventilation mask, and a positive end-expiratory pressure (PEEP) control port. A PEEP adjustor cap is connected to the PEEP control port, the PEEP adjustor cap having a bypass hole to allow gas to exit the T-piece and configured such that when the bypass hole is closed substantially all gas received at the air supply connection port is directed to the neonate, and when the bypass hole is open at least a portion of the gas received at the air supply connection port exits through the bypass hole. The T-piece is configured such that the bypass hole can be closed to deliver a sustained breath procedure to a neonate. A sustained breath delivery timer configured to limit a duration of the sustained breath procedure.

24 Claims, 8 Drawing Sheets

(51) Int. Cl.
*A61M 16/06* (2006.01)
*A61M 16/20* (2006.01)

(52) U.S. Cl.
CPC ... *A61M 16/201* (2014.02); *A61M 2016/0027* (2013.01); *A61M 2205/18* (2013.01); *A61M 2240/00* (2013.01)

(56) References Cited

U.S. PATENT DOCUMENTS

| | | | |
|---|---|---|---|
| 2009/0139522 A1* | 6/2009 | Thomson | A61M 16/209 128/204.22 |
| 2010/0206310 A1* | 8/2010 | Matsubara | A61M 16/209 128/205.24 |
| 2014/0150796 A1* | 6/2014 | Milne | A61M 16/024 128/205.23 |
| 2014/0275820 A1* | 9/2014 | Varga | A61M 16/0084 600/300 |
| 2015/0075524 A1* | 3/2015 | Millar | A61M 16/0666 128/203.27 |
| 2016/0166795 A1* | 6/2016 | Belsinger, Jr. | A61M 16/0833 128/204.26 |
| 2016/0346500 A1* | 12/2016 | Howe, Jr. | A61M 16/201 |
| 2018/0311461 A1 | 11/2018 | Walsh et al. | |

OTHER PUBLICATIONS

CA application 3136714 filed Apr. 17, 2020—Examiner's Report issued Jan. 19, 2023, 4 pages.

* cited by examiner

SYSTEMS AND METHODS FOR SUSTAINED BREATH DELIVERY TO NEONATES

CROSS-REFERENCE TO RELATED APPLICATIONS

This application is the U.S. national stage application of International Application PCT/US20/28759, filed Apr. 17, 2020, which international application was published on Oct. 29, 2020, as International Publication WO 2020/219360 A1 in the English language. The International Application claims priority to U.S. Provisional Patent Application No. 62/839,383 filed Apr. 26, 2019.

BACKGROUND

The present disclosure generally relates to systems and methods for providing respiratory care to neonates, and more particularly to systems and methods for performing a sustained breath procedure to a neonate immediately upon delivery.

A meta-analysis of randomized trials comparing noninvasive respiratory support in the delivery room with continuous positive airway pressure (CPAP) against intubation and ventilation showed that CPAP is associated with a reduced risk of bronchopulmonary dysplasia (BPD) or death. Continuous positive airway pressure (CPAP) has been used for respiratory support in premature infants and, when it is started at or soon after birth with subsequent selective surfactant administration, may be considered as an alternative to routine intubation with prophylactic or early surfactant administration in preterm infants.

In extremely preterm infants requiring resuscitation at birth, sustained inflation is often used at the beginning of CPAP, and is standard practice in some parts of the world. For preterm infants, and especially those less than 36 weeks postmenstrual age, the lungs are not fully developed and the respiratory muscles are weak. These preterm infants typically have weak respiratory muscles and fluid in their lungs, and thus struggle to aerate their lungs. Sustained inflation may be performed immediately upon birth to open the neonate's lungs and initiate respiration. Right after birth, for the first airflow, clinicians may perform a sustained inflation procedure.

SUMMARY

In one embodiment, a T-piece for ventilating a neonate includes a body having three ports, including an air supply connection port configured to connect to an air supply hose to receive gas therefrom, a mask connection port configured to connect to a neonatal ventilation mask, and a positive end-expiratory pressure (PEEP) control port. A PEEP adjustor cap is connected to the PEEP control port, the PEEP adjustor cap having a bypass hole to allow gas to exit the T-piece and configured such that when the bypass hole is closed substantially all gas received at the air supply connection port is directed to the neonate, and when the bypass hole is open at least a portion of the gas received at the air supply connection port exits through the bypass hole. The T-piece is configured such that the bypass hole can be closed to deliver a sustained breath procedure to a neonate. A sustained breath delivery timer configured to limit a duration of the sustained breath procedure.

A system for providing a sustained breath procedure to a neonate includes an air supply, a neonatal ventilation mask, and a T-piece for ventilating a neonate. The t-piece comprises a body having three ports, including an air supply connection port configured to connect to an air supply hose to receive gas therefrom, a mask connection port configured to connect to the neonatal ventilation mask, and a positive end-expiratory pressure (PEEP) control port. A PEEP adjustor cap is connected to the PEEP control port, the PEEP adjustor cap having a bypass hole to allow gas to exit the T-piece and configured such that when the bypass hole is closed substantially all gas received at the air supply connection port is directed to the neonate. When the bypass hole is open, at least a portion of the gas received at the air supply connection port exits through the bypass hole. The T-piece is configured such that the bypass hole can be closed to deliver a sustained breath procedure to a neonate. A sensor is configured to sense a condition within the T-piece and a controller is configured to identify occurrence of the sustained breath procedure based on the sensed condition and to limit a duration of the sustained breath procedure.

A method for controlling ventilation of a neonate includes sensing a condition within a T-piece ventilating a neonate, identifying with a controller occurrence of a sustained breath procedure based on the sensed condition, determining a recommended end time for the sustained breath procedure, and limiting a duration of the sustained breath procedure based on the recommended end time.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The inventors have recognized that, while sustained breath is an important procedure, systems and methods need to be developed to mitigate risks related to overexpansion of the lungs. Overextended peak inspiratory pressure (PIP) may cause lung overexpansion and diminish the benefits of CPAP. This is especially true for preterm infants, whose lungs are small and very fragile. It is especially important to avoid overinflating the lungs of these neonates, as doing so can cause alveolar burst, BPD, and/or otherwise traumatize the neonates' lungs. Thus, avoiding over inflation is important.

Figure 1A:
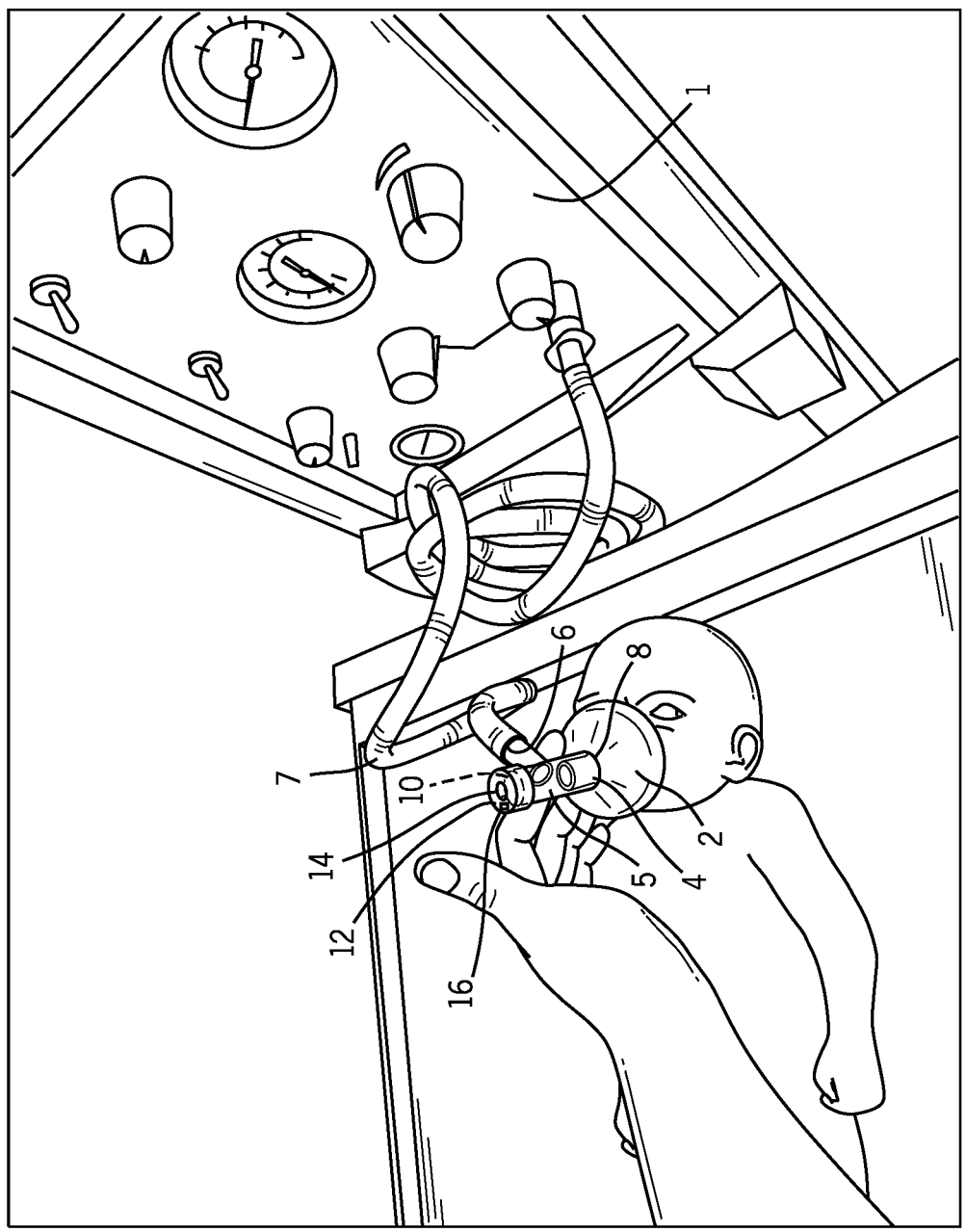
FIGS. 1A-1B depict performance of a sustained breath to a neonate in accordance with the present disclosure.
Figure 1B:
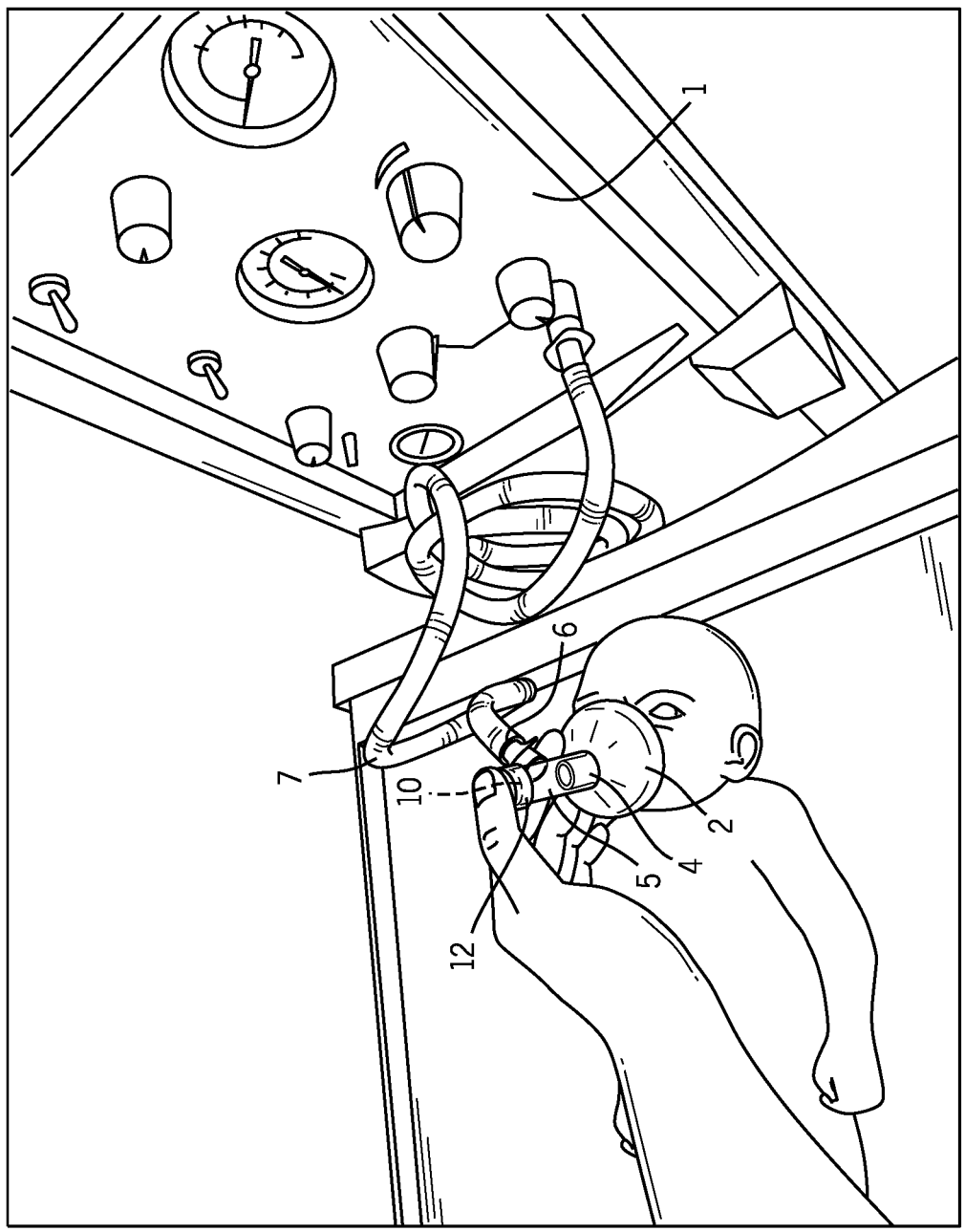

For performance of a sustained inflation procedure to a neonate, a neonatal ventilation mask is positioned over the neonate's nose and mouth, where the mask is connected to an air supply hose providing a mixture of $O_2$ and medical air. The CPAP system is configured to provide a positive gas pressure to the neonate, where a flow rate, pressure, and percent $O_2$ are controlled. FIGS. 1A and 1B demonstrate a system for ventilating the neonate and performance of a sustained breath procedure by a clinician. A T-piece 4 having a body 5 with three ports is provided. The body 5 may be, for example, a t-shaped body, or in other embodiments may be y-shaped, both of which are well known in the relevant art. The air supply hose 7 is connected to the neonatal ventilation mask 2 via a T-piece 4. The mask 2 is placed over the neonate's nose and mouth, as shown, where a T piece 4 connects between the mask 2 and the air supply hose 7. The air supply hose 7 connects to an air supply 1 controllable as described above. The T-piece 4 has three ports, including an air supply connection port 6 that connects to the air supply hose 7, a mask connection port 8 that connects to the mask 2, and a positive end-expiratory pressure (PEEP) control port 10. As is standard, a PEEP adjustor cap 12 is provided at the PEEP control port 10. The PEEP adjustor cap 12 has a bypass hole 14, or opening for expiration of breath. The PEEP adjustor cap 12 is used to adjust the minimum pressure (the PEEP pressure) to prevent the lungs from collapsing. Specifically, the PEEP adjustor cap 12 is adjustable to control an outflow pressure to control PEEP. When bypass hole 14 is covered, or otherwise closed, all air is directed from the air supply 1 to the neonate. When the bypass hole 14 is uncovered, or open, much of the supplied air bypasses the mask 2 and exits through the hole 14.

For the sustained inflation, the bypass hole 14 is blocked so that all air is directed to the neonate's lungs. For example, the clinician may block, or close off, the bypass hole 14 by placing their finger over the back of the cap 12 to cover the hole (see FIG. 1B). Peak inspiratory pressure (PIP) is delivered for an identified period of time, such as between two and ten seconds. The procedure clears fetal fluids from the neonate's lungs, opens the alveoli, and assists with additional neonate physiological needs. This is performed once as an initial breath and, typically, is not re-performed on a neonate. Embodiments of the disclosed system and method for safe performance of a sustained breath procedure are described herein which limit a duration of performance of the sustained breath procedure so as to avoid overexpansion of the neonate's delicate lungs.

Medical research has shown that over-sustained PIP can cause multiple medical issues in infants. Due to unique individual neonate physiology and lung capacity differences between neonates, the optimum time for an airflow application may vary. Likewise, the threshold period for over delivery of sustained inflation will also vary between neonates. However, if air is delivered for more than ten seconds, over inflation is likely. In the delivery environment, clinicians can (and do) lose track of PIP delivery time during a sustained breath procedure and inadvertently cause damage to the neonate's lungs.

Accordingly, the inventors have recognized a need for an improved system and method for assisting with and/or administering sustained inflation procedures to neonates. The inventors have recognized that these procedures are delivered to neonates in a busy and stressful environment where clinicians are required to perform multiple detailed tasks at once in a high-stress and chaotic environment. Sustained inflation delivery is typically a manual process where the clinician manually covers the bypass hole for a period of time. The inventors have recognized that systems and methods should be developed to assist a clinician with determining how long PIP is being delivered and whether PIP is being delivered for too long.

Accordingly, the inventors have recognized a need for a T-piece and mask system that provides feedback to a clinician to help them recognize when positive pressure has been applied for too long, which in various embodiments described herein may be more than a preset time or may be based on pressure measurements relating to the air delivery to the infant. In other embodiments, the system may be configured to automatically terminate PIP delivery after a predetermined administration time during a sustained breath procedure. In the various embodiments disclosed herein, the negative effects of overextending sustained inflation, such as alveolar burst and/or BPD, can be reduced or avoided.

A sustained breath delivery timer 16 is incorporated into the T-piece 4 and is configured to limit the delivery time of PIP for the sustained breath procedure. FIG. 1A depicts an embodiment having the sustained breath delivery timer 16 in the PEEP adjustor cap 12, but in other embodiments the sustained breath delivery timer 16 may be incorporated elsewhere in the T-piece 4 (e.g., in the body 5) or mask 2. FIGS. 2-6 depict exemplary embodiments of a sustained breath delivery timer 16, and functions thereof, for facilitating and limiting a sustained breath procedure. In certain embodiments, a sensing mechanism is provided to determine when the sustained inflation begins—i.e., when PIP is initiated. A timing mechanism monitors the duration of PIP administration and determines when PIP should be concluded, either based on passage of a predetermined period or based on pressure measurements relating to activity within the neonate's lungs. In other embodiments, sustained breath delivery timer 16 may be a mechanical valve or other mechanism for mechanically detecting and/or timing the duration of PIP delivery.

To limit the sustained breath, and thus conclude administration of PIP to avoid potential lung damage to the neonate due to overexpansion, the system may generate an alert to the clinician to conclude PIP administration, may automatically open a second bypass outlet, and/or may stop air flow to automatically cease PIP administration. In certain examples shown herein, the t-piece 4 is equipped with a mechanism for sensing whether the bypass hole 14 is closed, and thus whether inspiratory pressure is applied and the sustained breath procedure has started. A timer is then started to track the amount of time that the inspiratory pressure is provided. The timer is connected to an alarm or alert device on or in the vicinity of the mask and/or T-piece, and an alert is generated once inspiratory pressure is provided for a threshold amount of time. The alert indicates to the clinician to immediately remove the inspiratory pressure, such as removing their finger from the bypass hole 14. Alternatively, a valve or other bypass mechanism may be automatically opened to instantly release pressure on the neonate's airway, thus providing immediate conclusion of the sustained inflation.

Figure 2:
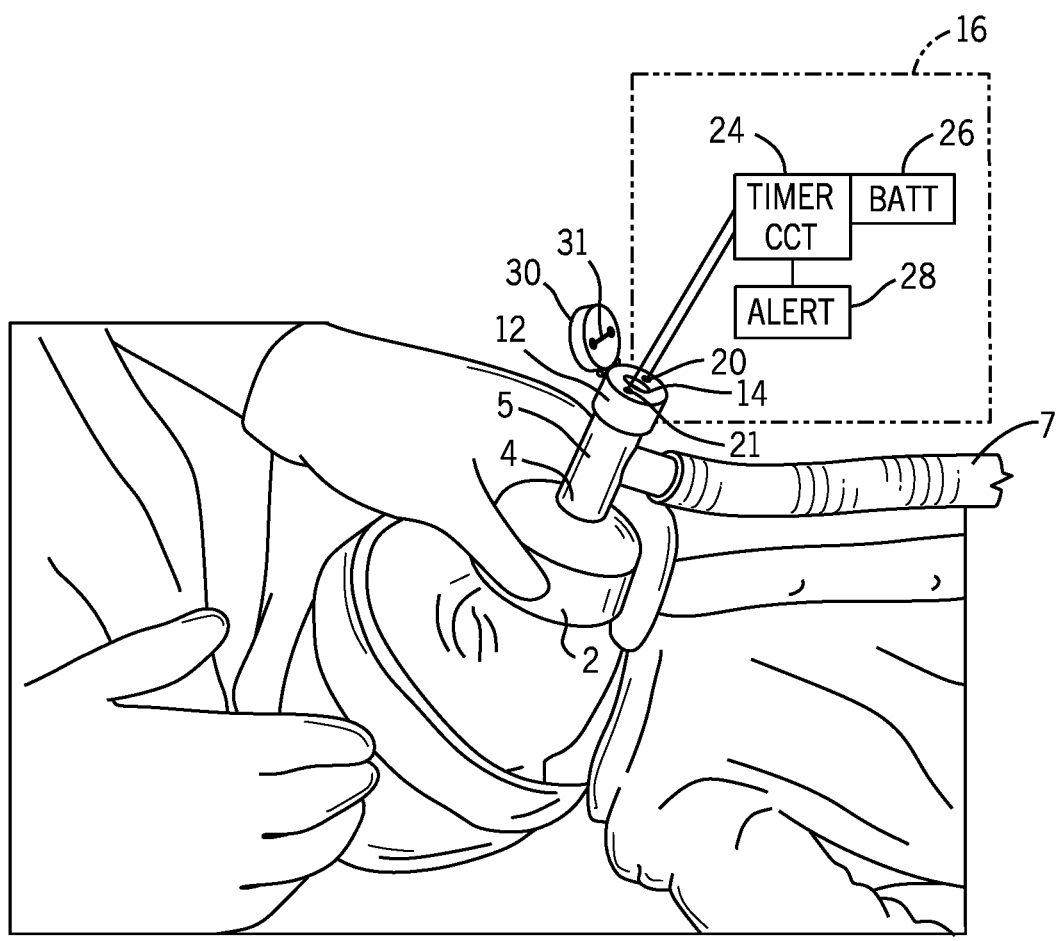
FIG. 2 schematically depicts one embodiment of a system for providing a sustained breath procedure in accordance with the present disclosure.
Figure 3:
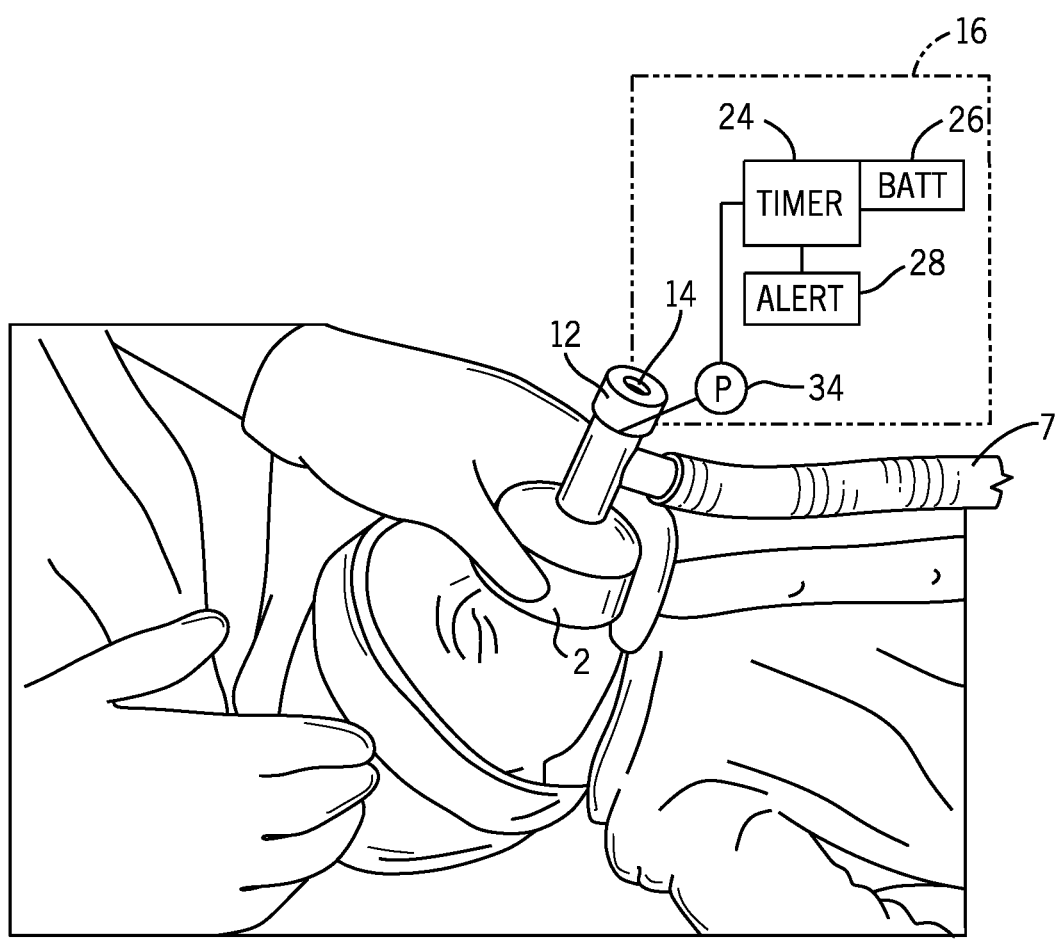
FIG. 3 schematically depicts another embodiment of a system for providing a sustained breath procedure in accordance with the present disclosure.

In FIG. 2, a system is provided that senses when the bypass hole 14 is closed, which indicates a start of the sustained breath procedure, and provides a timed notification to alert a clinician of when a recommended delivery period ends, thus providing a latest recommended end time of when the inspiratory pressure should be immediately released. In the depicted example a contact sensor is provided around the bypass hole such that covering the bypass hole 14 is sensed. Two contacts 20 and 21 are provided on the PEEP adjustor cap 12, such as on either side of the bypass hole 14. These contacts 20, 21 connect to a timer circuit 24 configured to track a period that the bypass hole 14 is closed. For example, the timer circuit may include an RC circuit or an RLC circuit powered by a battery 26. For example, the timer circuit 24 may include a selectively-sized capacitor that would delay activation of the alert device 28 by a predetermined amount of time. In certain embodiments, the timer circuit 24 may include a current dump resistor to drain the capacitor once the circuit opens, effectively resetting the preset time of the timer circuit 24. Thus, so long as the battery 26 has sufficient remaining charge, the system can be reactivated to monitor sustained inflation. The timer circuit 24 may be designed to provide a predetermined amount of delay, as may be needed in order to provide a predetermined inspiratory pressure for a recommended maximum amount of time before generating an alarm via the alert 28. In various embodiments, the predetermined amount of time, and thus the recommended end time for a sustained breath procedure, may be some amount of time between two and ten seconds, such as two seconds, three seconds, or five seconds, etc. Alternatively, in some embodiments, the timer circuit may be a microcontroller. In an embodiment where the timer circuit 24 includes a microcontroller, the predetermined amount of time, and thus the recommended end time for the sustained breath procedure, may be adjustable.

When the bypass hole 14 is uncovered, the contacts 21 and 22 are an open circuit such that no current flows through the timer circuit. When the bypass hole 14 is covered, the contact points 21 and 22 are shunted and current can flow through the timer circuit 24. Namely, current is permitted to flow from the battery 26 through the timer circuit 24, which includes contact points 20 and 21, and eventually to the alert element 28. At the end of the predetermined time period, current is shunted to the alert device 28.

In various examples, the alert may be a visual alert, an auditory alert, or a haptic alert. For example, the alert device 28 may include piezoelectric buzzer or beeper, or a speaker to provide an auditory alert or an alarm at the end of the predetermined period. Alternatively or additionally, the alert device 28 may include an LED or other visual feedback device that can provide a visual alert to the clinician at the end of the predetermined period. In some other environments, the alert device 28 may include a haptic feedback element, such as a vibrating element that vibrates at the end of the predetermined period. The battery 26 may be, for example, a button cell battery. The battery may be relatively small and may be configured to power the timer circuit 24 and alert 28 for only one use or only a few uses. Since the sustained inflation procedure is only performed once, the system does not need to be designed for multiuse. In other embodiments, the system may be designed for performance of at least a few sustained inflation procedures. This may be necessary where a test procedure was initially performed to test the pressure (such as on the clinician's hand), and thus the timer circuit must be reset.

In certain embodiments, the flap 30 or covering element may be provided that can be closed over the end of the cap 12 in order to close off the bypass hole 14. FIG. 2 exemplifies one embodiment having a flap 30. The flap 30 may include a conductive track 31 positioned such that, when the flap 30 is closed, the conductive track 31 makes contact with the electrical contacts 20 and 21 in order to close the timer circuit 24. The flap 30 may be spring loaded and biased towards the open position such that it only remains closed while the clinician holds it shut, such as by holding their finger on top of the flap to keep it in contact with the cap 12, and immediately opens once the force is removed. In other embodiments, the contacts 20, 21 may be arranged such that a clinician's finger over the bypass hole 14 closes the circuit. Thus, the need for a flap or other closing device is negated and the timer will be initiated once the clinician places their finger at the end of the cap 12 in order to close off the bypass hole 14.

In another embodiment, the pressure sensor 34 may be provided in the T-piece, such as at or near the PEEP control port 10 and cap 12. The pressure sensor 34 senses a pressure within the T-piece. When the bypass hole 14 is closed, the pressure will remain almost constant while the lungs inflate. Once the threshold pressure is sensed by the pressure sensor 34 during the ongoing sustained breath procedure, the timer circuit 24 may be activated. For example, a high threshold pressure sensor 34 may be connected to a relay in the timer circuit 24, either by logic or by an analog circuit. When the threshold pressure is sensed, a relay within the timer circuit 24 is closed in order to allow current to flow through the timer circuit 24. The alert device 28 is activated after a predetermined time, as described above. The predetermined time is associated with a maximum time that the high pressure portion of the sustained breath procedure should be maintained, and thus a latest recommended end time for the procedure.

In certain embodiments, the timer may activate a bypass valve or otherwise open a second bypass outlet to automatically open the airway circuit after the predetermined amount of time. Such an automatically-controlled bypass valve may be provided as an alternative to the alert device 28, or in addition to the alert device 28. For example, the timer circuit 24 may activate a solenoid that opens a bypass valve connected to a second port which connects the inside of the T-piece 4 to the outside environment so that the pressure inside the T-piece can be automatically and immediately reduced at the end of the predetermined period. The bypass valve will allow pressure to escape from the T-piece 4, performing the same function as the bypass hole 14. Thus, the system does not wait for the clinician to open the bypass hole 14, such as by removing their finger, in response to an alert. Instead, at the end of the predetermined time period, the pressure is immediately released through the bypass valve and patient safety is ensured. The bypass valve may be configured to automatically reset, or may require manual resetting to close the bypass valve so that the PEEP adjustor cap 12 can function normally.

In yet another embodiment, a spring-loaded impeller device may be included that projects into the airstream between the bypass hole 14 or other relief valve and the mask 2. The spring-loaded impeller rotates a fixed number of degrees per cubic centimeter of flow through the T-piece 4. The spring-loaded impeller is connected by a shaft to a switch. After a predetermined number of degrees of rotation, the switch is mechanically and electrically closed, which shunts current to the alert device 28 (or to a solenoid that opens a bypass valve). The alert device 28 may continue to be activated until the spring-loaded impeller device returns to its initial position.

Figure 4:
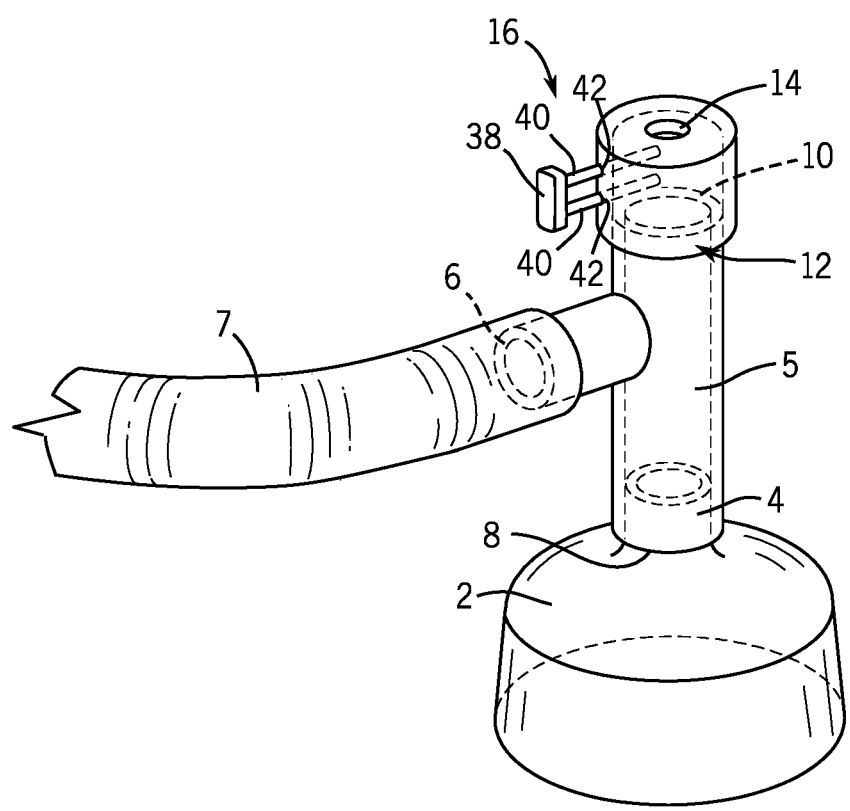
FIG. 4 depicts an embodiment of a T-piece in another embodiment of a system for providing a sustained breath procedure in accordance with the present disclosure.

FIG. 4 depicts another embodiment where the sustained breath delivery timer 16 is a mechanical bypass valve 38 is provided, such as in the cap 12. In other embodiments, the bypass valve 38 may be located elsewhere on the T-piece 4 so long as it is within a constant static pressure region at and around the PEEP control port 10 end of the T-piece 4. In the depicted example, the bypass valve 38 is a mechanical device configured to open in response to pressure and time. The mechanical bypass valve 38 may be configured such that it opens after the predetermined amount of time when subjected to the expected inspiratory pressure. Expected inspiratory pressure varies per the neonate gestational age and alveolar development. PIP pressure may be set by a clinician, which on many systems may range from 0 to 8 kPa. The normal neonatal lung may require more than the 15 cm H2O (11.5 mm Hg) permitted on most positive-pressure resuscitation devices. In certain embodiments, the valve may be adjustable to set the expected inspiratory pressure and dwell time. In other embodiments, different T-pieces may be available and selected based on gestational age and/or development. In certain embodiments, the valve may be adjustable to set the expected inspiratory pressure, in other embodiments different t-pieces may be available and selected based on gestational age and development. Thus, when the bypass hole 14 is closed and the pressure inside the T-piece is at the expected inspiratory pressure, the mechanical bypass valve 38 may begin to open and may continue to slide open so long as the inspiratory pressure is maintained for the predetermined amount of time. Thereby a second bypass valve is opened to immediately release at least some of the pressure in the T-piece, even if the clinician does not open the main bypass hole. Various valve mechanisms may be used for this purpose.

In the depicted example, the mechanical bypass valve 38 includes at least one prong 40 of a predetermined length and having a predetermined frictional arrangement with a respective hole or orifice. The prongs 40, or valve seat, is/are subjected to the pressure inside the T-piece 4. The prongs 40 are configured such that the bypass valve 38 is pushed open at a predetermined rate when exposed to the predetermined inspiratory pressure. Depending on the length of the prongs 40 and the rate at which they are pressed outward, the duration of pressure exposure until the valve 38 opens can be controlled. The prong(s) 40, or valve seat, is sized and has a length according to the time needed for a successful procedure (e.g. not more than 10 seconds). Once the valve 38 is pushed sufficiently outward, the bypass port opens and pressure is released from the T-piece 4. Thereby, the mechanical bypass valve 38 can act as a timer to release pressure after a predetermined amount of time.

Figure 5:
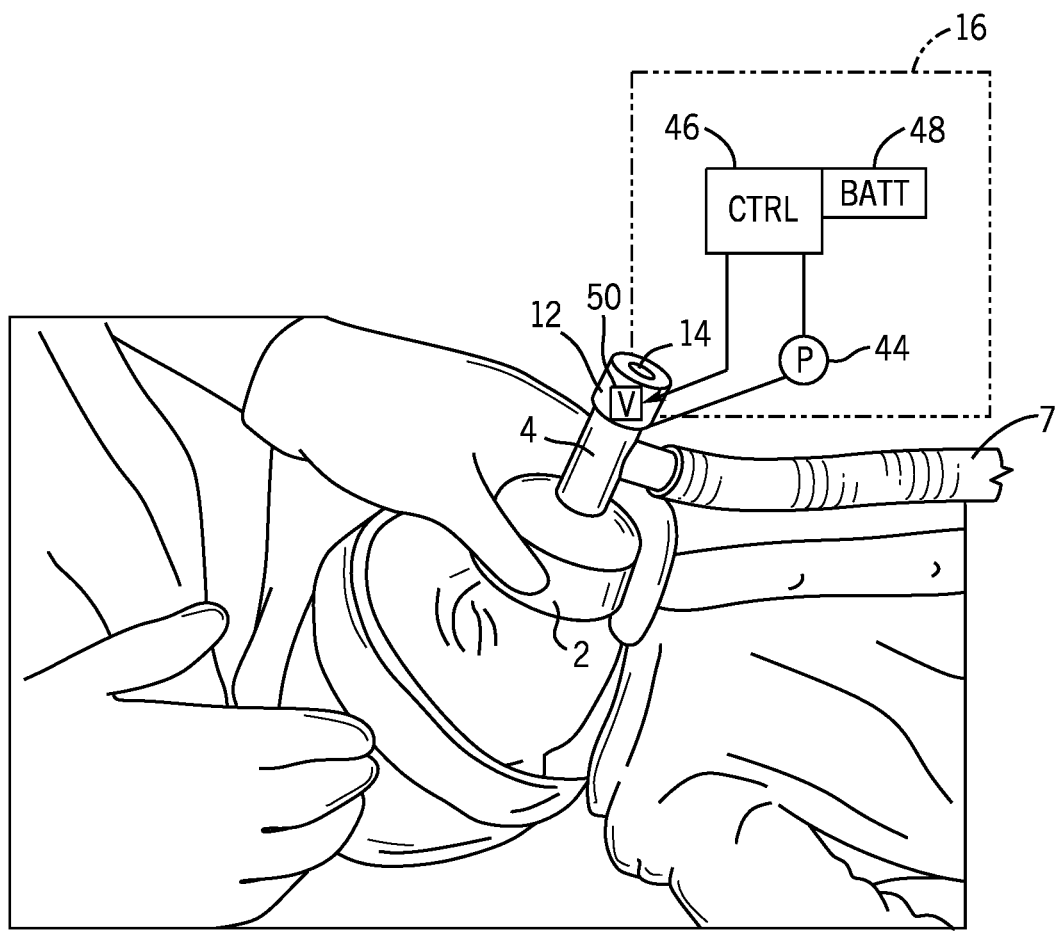
FIG. 5 schematically depicts another embodiment of a system for providing a sustained breath procedure in accordance with the present disclosure.

FIG. 5 depicts another embodiment having a sustained breath delivery timer 16 including a pressure sensor. The inventors have recognized that the system can be designed to detect successful completion of the sustained inflation procedure—i.e., when the alveoli are opened. Because each infant has a different physiology, a predetermined time may not be the most effective way to administer the sustained inflation. Accordingly, the inventors have developed a device that continuously monitors pressure in the T-piece 4, and thus the pressure being administered to the infant, and looks for a predetermined pressure pattern indicating that the procedure is successful and thus should be ended. In various examples, the predetermined pressure pattern may be a threshold pressure value that is sustained or exceeded for at least a predetermined time, may be an identified pressure peak, may be a threshold decrease in pressure within a threshold time period, may be a pressure minimum following a pressure peak, or may be based on some other detectable sequence or behavior of sensed pressure values inside the t-piece.

Figure 6:
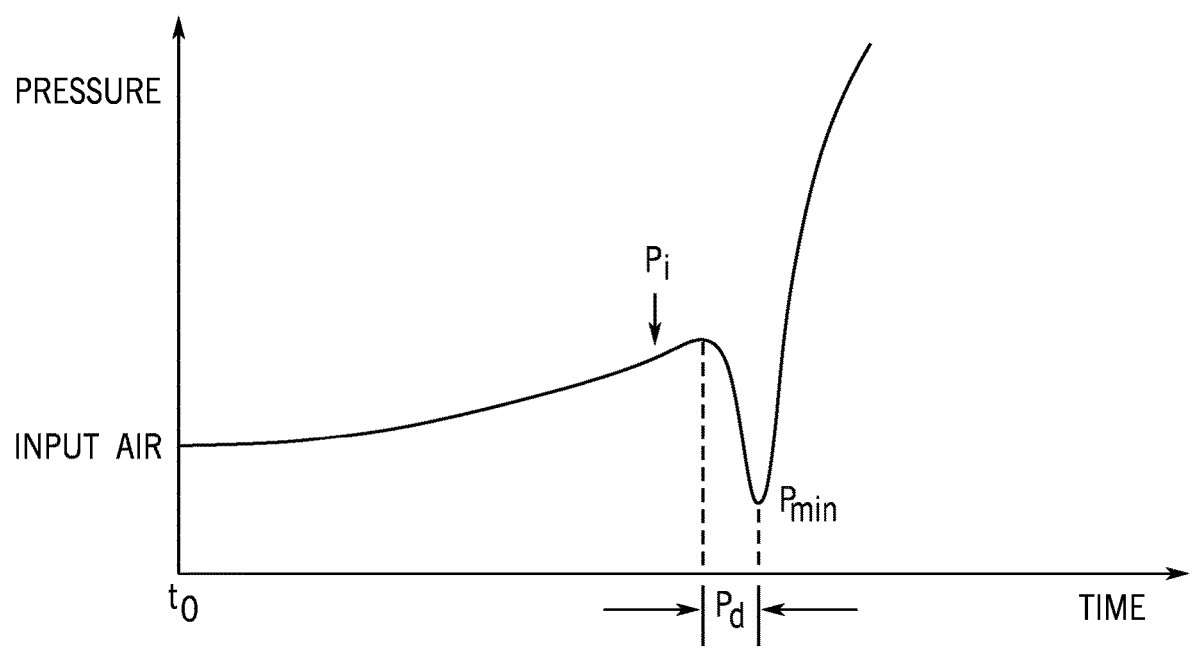
FIG. 6 is a graph showing pressure in a T-piece during a sustained breath procedure.

FIG. 6 is a graph depicting pressure changes over time in an exemplary sustained inflation procedure. The bypass hole 14 and/or other bypass valves are closed at time $t_0$. The pressure within the T-piece 4 reaches the expected constant pressure and stays almost constant as the lungs of the infant inflate. The pressure builds and increases slightly as the clogged alveoli resist opening. Around the location labeled $P_i$ in the graph, the pressure increases slightly and reaches a maximum before quickly falling to a minimum (the region marked $P_d$). Because the alveoli are clogged with fluid, and thus represent a clogged system, the pressure minimally raises before the lungs are cleared, and then quickly drops once the alveoli open. Once the pressure reaches the minimum point where the alveoli are open, $P_{min}$, the pressure quickly rises thereafter. This is where damage to the infant's lungs occurs. The inventors have recognized that portions of this pressure pattern, such as features of the pressure drop, can be detected and indicate success of the procedure and a recommended end time therefor. Upon detection of success, the system can be controlled to immediately relieve the pressure to avoid any adverse effect to the infant's lungs. Thereby, a dangerous pressure increase can be avoided.

In one embodiment, the pressure sensor 44 continually measures pressure within the T-piece 4 and provides pressure measurements to the controller 46. The controller 46, which includes a processor, executes logic to detect the pressure drop indicating successful completion of the procedure. For example, the controller 46 may execute falling edge detection logic to detect initiation of the pressure drop in region $P_d$. In other embodiments, the controller 46 may be configured to detect a threshold pressure decrease over a predetermined amount of time. In still other embodiments, the controller 46 may be configured to detect the pressure minimum $P_{min}$, such as by a rising edge detection algorithm or a peak detection algorithm. In other embodiments, the successful completion is measured and detected based on a pressure differential from two pressure sensors, one measuring an input pressure (e.g. at or near the air supply connection port 6) and the other measuring a delivered pressure (e.g. at or near the mask connection port 8).

Once the pressure pattern is detected, such as the above-described thresholds or features, the controller 46 may control one or more devices to immediately release or reduce the pressure being applied to the infant's airway. In one embodiment, the controller 46 may generate a control instructions to open a second bypass outlet (e.g., bypass valve 50), such as by directly controlling operation of the valve or by activating current flow to a solenoid as described above. In certain examples, the bypass valve 50 may be incorporated into the bypass hole 14, such as where the system is arranged such that the clinician does not cover the bypass hole 14 with their finger but the valve is closed (such as manually closing it by a button or electrically activating closure). In other embodiments, the bypass valve 50 may be a separate bypass channel than the bypass hole 14. In still other embodiments, the controller 46 may control an air supply shutoff to stop the flow of air into the mask 2. By either means, the air input to the infant's lungs is immediately ceased once the pressure fluctuation defining a successful procedure is detected.

Figure 7:
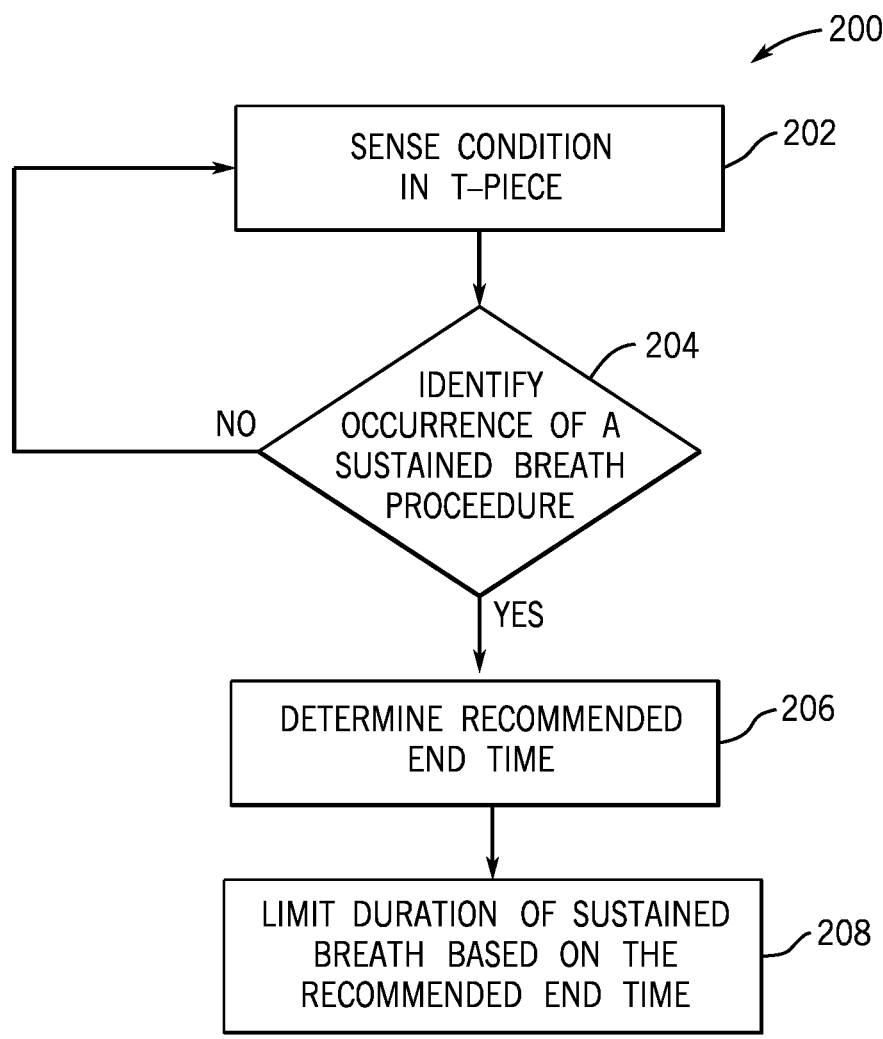
FIG. 7 is a flow chart exemplifying one embodiment of a sustained breath procedure.

FIG. 7 is a method diagram exemplifying a method 200 of controlling ventilation of a neonate to deliver a sustained breath procedure. A condition within the T-piece 4 is sensed at step 202, wherein the condition within the T-piece 4 can be monitored to determine when a sustained breath procedure is occurring. As described herein, the sensed condition may be pressure within the T-piece 4. In another embodiment, the sensed condition indicating occurrence of the sustained breath procedure may be covering or otherwise closing the bypass opening 14 such that PIP is delivered to the neonate. In still other embodiments, sensing the occurrence of the sustained breath procedure may be by a spring loaded impeller configured to trigger the timer circuit, as is described above. Once the condition indicating the sustained breath procedure is detected at step 204, a recommended end time for the sustained breath procedure is determined at step 206. For example, the recommended end time may be a predetermined time after the detection of the occurrence of the sustained breath procedure. In another embodiment, the recommended end time may be upon the occurrence of a predetermined pressure pattern in the pressure curve measured during the sustained breath procedure, examples of which are described above with respect to FIG. 6. Once the recommended end time for the procedure is reached, one or more steps are taken to limit the duration of the procedure. For example, an alert may be generated to inform or instruct the clinician to stop the procedure, such as by remove their finger from the bypass opening 14. Alternatively or additionally, limiting the duration of the procedure may include opening a second bypass valve to immediately release pressure from inside the T-piece, and thus immediately reduce the inspiratory pressure delivered to the infant and allow exhalation to proceed.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The scope of the invention may include other examples that occur to those skilled in the art. Such other examples are intended to be within the scope of the disclosure if they have features, functions, or structural elements that do not differ from the embodiments disclosed herein, or if they include equivalent features or structural elements with insubstantial differences from the literal languages of the disclosed embodiments.

We claim:

1. A T-piece for ventilating a neonate, the t-piece comprising:
    a body including an air supply connection port configured to connect to an air supply hose to receive gas therefrom, a mask connection port configured to connect to a neonatal ventilation mask, and a positive end-expiratory pressure (PEEP) control port;
    a PEEP adjustor cap connected to the PEEP control port, the PEEP adjustor cap having a bypass hole to allow gas to exit the T-piece and configured such that when the bypass hole is closed substantially all gas received at the air supply connection port is directed to the neonate, and when the bypass hole is open at least a portion of the gas received at the air supply connection port exits through the bypass hole;
    at least one sensor configured to sense a condition within the T-piece;
    wherein the T-piece is configured such that the bypass hole can be closed to deliver a sustained breath procedure to a neonate; and
    a sustained breath delivery timer configured to limit a duration of the sustained breath procedure and wherein the sustained breath delivery is controlled based on the duration and the sensed condition.

2. The T-piece of claim 1, wherein the at least one sensor includes a pressure sensor configured to sense a pressure in the body and further comprising a controller configured to receive the sensed pressure from the pressure sensor and to limit the duration of the sustained breath based thereon.

3. The T-piece of claim 2, wherein the controller is configured to detect a predetermined pressure pattern and to limit the duration of the sustained breath upon detection of the predetermined pressure pattern.

4. The T-piece of claim 3, wherein the predetermined pressure pattern is a threshold pressure drop representing opening alveoli in lungs of the neonate.

5. The T-piece of claim 3, wherein the predetermined pressure pattern is a pressure minimum following a threshold pressure drop representing opening alveoli in lungs of the neonate.

6. The T-piece of claim 3, wherein the predetermined pressure pattern is the pressure in the body being at least a threshold pressure for a threshold period of time.

7. The T-piece of claim 1, wherein the at least one sensor includes at least two pressure sensors configured to sense pressure at two different locations in the body and further comprising a controller configured to determine a pressure differential between the sensed pressures at the two different locations and to limit the duration of the sustained breath based on the pressure differential.

8. The T-piece of claim 1, wherein the at least one sensor includes a contact sensor configured to sense when the bypass hole is closed and wherein the sustained breath delivery timer is configured to track a period that the bypass hole is closed.

9. The T-piece of claim 8, wherein the contact sensor comprises two contacts, one on either side of the bypass hole, and further comprising a spring-loaded flap connected to the PEEP adjustor cap, wherein the spring-loaded flap is biased open and is manually closable by a clinician to cover the bypass hole, wherein the flap has a conductive track that electrically connects the two contacts when the flap covers the bypass hole.

10. The T-piece of claim 1, wherein the least one sensor includes a pressure sensor configured to sense a pressure in the body.

11. The T-piece of claim 1, wherein limiting the duration of the sustained breath includes effectuating at least one of: opening a second bypass valve to allow gas to exit the T-piece and stopping gas flow from the air supply.

12. The T-piece of claim 1, wherein limiting the duration of the sustained breath includes generating an alert instructing a clinician to open the bypass hole.

13. The T-piece of claim 1, sustained breath delivery timer includes a mechanical timer valve configured to open once a pressure in the body is at least a threshold pressure for a threshold time.

14. The T-piece of claim 13, wherein the mechanical timer valve includes at least one prong in frictional engagement with and blocking a second bypass outlet, wherein the threshold pressure is an expected inspiratory pressure for the neonate, wherein the prong and bypass outlet are configured such that when the pressure in the body is at least the expected inspiratory pressure the prong is forced outward at a predetermined rate, wherein the prong has a length configured to block the second bypass outlet for the threshold time while the pressure in the body is at least the expected inspiratory pressure.

15. A system for providing a sustained breath procedure to a neonate, the system comprising:
    an air supply;
    a neonatal ventilation mask;
    a T-piece for ventilating a neonate, the t-piece comprising
        a body including an air supply connection port configured to connect to an air supply hose to receive gas therefrom, a mask connection port configured to connect to the neonatal ventilation mask, and a positive end-expiratory pressure (PEEP) control port;
        a PEEP adjustor cap connected to the PEEP control port, the PEEP adjustor cap having a bypass hole to allow gas to exit the T-piece and configured such that when the bypass hole is closed substantially all gas received at the air supply connection port is directed to the neonate, and when the bypass hole is open at least a portion of the gas received at the air supply connection port exits through the bypass hole;

wherein the T-piece is configured such that the bypass hole can be closed to deliver a sustained breath procedure to a neonate; and a sensor configured to sense a condition within the T-piece;

a controller configured to identify occurrence of the sustained breath procedure based on the sensed condition and to limit a duration of the sustained breath procedure.

16. The system of claim 15, wherein the sensor includes a pressure sensor configured to sense a pressure in the body and wherein the controller is configured to detect a predetermined pressure pattern and to limit the duration of the sustained breath based on detection of the predetermined pressure pattern.

17. The system of claim 16, wherein the predetermined pressure pattern is a threshold pressure drop representing opening alveoli in lungs of the neonate.

18. The system of claim 16, wherein the predetermined pressure pattern is a pressure minimum following a threshold pressure drop representing opening alveoli in lungs of the neonate.

19. The system of claim 16, wherein the predetermined pressure pattern is the pressure in the body being at least a threshold pressure for a threshold period of time.

20. The system of claim 16, further comprising at least two pressure sensors configured to sense pressure at two different locations in the body and wherein the controller is configured to determine a pressure differential between the sensed pressures at the two different locations and to limit the duration of the sustained breath based on the pressure differential.

21. The system of claim 15, wherein the sensor includes a contact sensor configured to sense when the bypass hole is closed and a timer configured to track a period that the bypass hole is closed.

22. The system of claim 15, wherein the controller is configured to limit the duration of the sustained breath by generating a control signal to open a second bypass valve to allow gas to exit the T-piece.

23. The system of claim 15, wherein the controller is configured to limit the duration of the sustained breath by generating a control signal to stop gas flow from the air supply.

24. The system of claim 15, wherein the controller is configured to limit the duration of the sustained breath by operating a user interface to generate an alert instructing a clinician to open the bypass hole.

* * * * *